(12) United States Patent
Ballinger, Jr. et al.

(10) Patent No.: US 6,309,597 B1
(45) Date of Patent: Oct. 30, 2001

(54) METHOD FOR REDUCING HYDROGEN SULFIDE LEVEL IN WATER CONTAINING SULFATE-REDUCING BACTERIA AND HYDROGEN SULFIDE-METABOLIZING BACTERIA

(75) Inventors: Kenneth E. Ballinger, Jr., Kennett Square, PA (US); Edward D. Burger, Plano, TX (US); Robert F. Knauer, Claremont, CA (US)

(73) Assignee: Arkion Life Sciences, Wilmington, DE (US)

( * ) Notice: Subject to any disclaimer, the term of this patent is extended or adjusted under 35 U.S.C. 154(b) by 0 days.

(21) Appl. No.: 09/228,385

(22) Filed: Jan. 12, 1999

Related U.S. Application Data

(63) Continuation-in-part of application No. 08/854,828, filed on May 12, 1997, now abandoned, and a continuation-in-part of application No. 08/901,884, filed on Jul. 29, 1997.

(51) Int. Cl.[7] .............................. C23F 11/12; C02F 1/68
(52) U.S. Cl. ................. 422/28; 422/14; 210/764
(58) Field of Search ................... 422/16, 14, 5, 422/28; 210/764

(56) References Cited

U.S. PATENT DOCUMENTS

| | | | |
|---|---|---|---|
| 3,300,404 | 1/1967 | Howe et al. | 210/610 |
| 4,446,031 | 5/1984 | List | 252/1 |
| 4,680,127 | 7/1987 | Edmondson | 422/5 X |
| 4,681,687 | 7/1987 | Monche et al. | 422/28 X |
| 4,911,843 | 3/1990 | Hunniford et al. | 210/610 |
| 5,385,844 | 1/1995 | Kennamer et al. | 436/13 |
| 5,500,368 | 3/1996 | Tatnall | 435/262 |

FOREIGN PATENT DOCUMENTS

| | | | |
|---|---|---|---|
| 576124-A1 | * | 12/1993 | (EP) . |
| 591000-A1 | * | 4/1994 | (EP) . |
| 08012503-A | * | 1/1996 | (JP) . |

* cited by examiner

*Primary Examiner*—Elizabeth McKane
(74) *Attorney, Agent, or Firm*—Basil S. Krikelis; Don O. Winslow

(57) ABSTRACT

A method for reducing the level of hydrogen sulfide in water containing sulfur-reducing bacteria and hydrogen sulfide-metabolizing bacteria by addition of an aqueous solution of metallic nitrogen oxides and small particles of water-insoluble polycyclic quinones.

9 Claims, No Drawings

METHOD FOR REDUCING HYDROGEN SULFIDE LEVEL IN WATER CONTAINING SULFATE-REDUCING BACTERIA AND HYDROGEN SULFIDE-METABOLIZING BACTERIA

RELATED APPLICATIONS

This application is a continuation-in-part of U.S. patent applications Ser. No. 08/854,828, filed May 12, 1997 now abandoned, and Ser. No. 08/901,884, filed Jul. 29, 1997.

BACKGROUND OF THE INVENTION

Uncontrolled microbial growth and activity can create severe optional, environmental, and human safety problems in wastewater treatment and handling systems associated with municipal, industrial and oilfield operations. Problems caused or intensified by microbial growth and activity include corrosion, solids production, and hydrogen sulfide ($H_2S$) generation. $H_2S$ not only has a highly offensive odor, but is toxic even in quite small concentrations. Though $H_2S$ is present in the air above wastewater in only small concentrations, it has been very difficult to reduce significantly in even the most efficiently operated water handling system.

The microorganisms primarily responsible for $H_2S$ generation in an anaerobic environment within municipal, industrial and oilfield water operations are sulfate-reducing bacteria. These organisms are ubiquitous and can grow in almost any environment. They are routinely found in waters associated with oil production systems and can be found in virtually all industrial aqueous processes, including cooling water systems, pulp and paper-making systems, chemical manufacturing, and petroleum refining.

Requirements for sulfate-reducing bacteria activity and growth include an anaerobic (oxygen-free) aqueous solution containing adequate nutrients, an electron donor and electron acceptor. A typical electron acceptor is sulfate, which Produces $H_2S$ upon reduction. A typical electron donor is a volatile fatty acid (e.g., acetic or propionic acids), although hydrogen can also function as an electron donor. Conditions in an oil reservoir subject to seawater flooding are excellent for establishing sulfate-reducing bacteria activity. Seawater contains a significant concentration of sulfate, while connate, or indigenous formation, water contains volatile fatty acids and other required trace nutrients (e.g., nitrogen and phosphorus). Conditions within industrial water systems, such as effluent streams from production operations or cooling water streams, are also conducive to sulfate-reducing bacteria activity due to the anaerobic biofilm which is formed on pipeline, tank or vessel walls. The same is true within the sewers and other piping and facilities associated with municipal wastewater handling systems.

Hydrogen sulfide is corrosive and reacts with metal surfaces to form insoluble iron sulfide corrosion products. In oilfield operations, $H_2S$ partitions into the water, oil and natural gas phases of produced fluids and creates a number of problems. For instance, oil and gas, which contain high levels of $H_2S$, have a lower commercial value than low sulfide oil and gas. Removing biogenic $H_2S$ from sour oil and gas increases the cost of these products. Hydrogen sulfide is an extremely toxic gas and can be immediately lethal to humans at even small concentrations. Its presence in wastewater systems poses a threat to worker safety. The discharge of produced waters containing high levels of $H_2S$ into aquatic or marine environments is hazardous because $H_2S$ reacts with oxygen and lowers the dissolved oxygen levels in the water.

Corrosion caused by sulfate-reducing bacteria and $H_2S$ frequently results in extensive damage. Pipe systems, tank bottoms and other pieces of equipment can rapidly fail if they have areas where microbial corrosion is occurring. If a failure occurs in a pipeline or storage tank bottom, the released fluid can have serious environmental consequences. If a failure occurs in a high pressure water or gas line, the consequences may be worker injury or death. Any such failure involves substantial repair or replacement costs.

In addition to such industrial problems with the generation of hydrogen sulfide, an altogether too familiar sensation in many communities having wastewater treating systems is the rotten egg smell of the gas hydrogen sulfide. Hydrogen sulfide ($H_2S$) is metabolic product of sulfate-reducing bacteria which are ordinarily contained in anaerobic wastewater streams. This gas not only has a highly offensive odor, but is toxic even in quite small concentrations. Though $H_2S$ is present in the air above wastewater in only small concentrations, it has been very difficult to reduce it significantly in even the most efficiently operated municipal and industrial wastewater treatment systems.

There are two basic approaches to reducing $H_2S$ in water systems. One approach to the problem of reducing $H_2S$ odor is to inhibit the production of $H_2S$ by various means within the water stream. The other approach is to remove the $H_2S$ produced in such streams.

As to the first method, it is known to add nitrates and/or nitrites to sewage to reduce biological oxygen demand (BOD) and to suppress the formation of $H_2S$ by bacterial action. (U.S. Pat. Nos. 3,300,404; 4,446,031 and 4,681,687). It is also known to add nitrates to sewage to control objectionable odors (U.S. Pat. No. 4,680,127).

As to the second method, in U.S. Pat. No. 4,680,127 is disclosed a method for removing $H_2S$ by addition of glyoxal and formaldehyde to scavenge $H_2S$ from aqueous gas streams. Also, U.S. Pat. No. 4,911,843 to Hunniford et al., discloses a method for removing dissolved $H_2S$ from sewage by the addition of aqueous solutions of inorganic nitrates to stimulate the growth of bacteria, which consume $H_2S$ metabolically. A different technique is taught by Tatnall in U.S. Pat. No. 5,500,368. This patent discloses the addition of very small amounts of finely divided particles of anthraquinones to a medium containing sulfate-reducing bacteria to inhibit production of $H_2S$ therein. U.S. Pat. No. 5,385,844 to Weimer et al., discloses inhibiting $H_2S$ production by sulfate-reducing bacteria by contacting the medium containing the sulfate-reducing bacteria with a wide variety of anthraquinone compounds.

While all of the foregoing methods for inhibiting the formation of $H_2S$ and for removing $H_2S$ are effective to some extent, none is wholly satisfactory because the efficiency of each is low and the relative cost of utilizing them is quite high. For that reason, applicants have sought an efficient and more cost-effective method for keeping the odor level of wastewater streams down to a safe level by a method which involves both keeping the production of $H_2S$ production low and removing whatever low amount of $H_2S$ is produced.

Jenneman et al. (Jenneman, G. E., McInerney, M. J. and Knapp, R. M., "Effect of nitrate on biogenic sulfide production", *Applied and Environmental Microbiology*, 51, No. 6, p. 1205, 1986) determined in laboratory studies that sulfide production was inhibited from sewage sludge, pond sediment and oil field brines upon treatment with nitrate. Their results supported the contention that prolonged inhibition of sulfide production is due to the increase in the redox potential of the environment as a result of the action of nitrate-using bacteria. Two different reasons for this effect were suggested: 1) the redox potential increased due to the buildup of $N_2O$ or NO or both, which resulted in an oxidized environment, and 2) the levels of sulfate-reducing bacteria decreased during the prolonged exposure to an oxidizing environment and high $N_2O$ concentration. The results also suggested that short-term inhibition of sulfide production was due to the preferential use of nitrate by the sulfate-reducing bacteria as an electron acceptor, although it was recognized that there was probably a competition among sulfate-reducers and denitrifying (nitrate-using) bacteria present in the waters utilized.

The use of nitrates and denitrifying bacteria to mitigate $H_2S$ production within an oilfield environment has been well documented. Sublette et al. (Sublette, K. L., Morse, D. E. and Raterman, K. Y., "A field demonstration of sour produced-water remediation by microbial treatment," *SPE Production & Facilities*, p. 183, August 1994 determined in an oil field pilot study that the addition of a sulfide-tolerant strain of the chemautotroph and facultative anaerobe *Thiobacillus denitrificans* and nitrate to an aerobic sour brine was able to almost instantly bio-oxidize the sulfide to elemental sulfur and sulfate.

U.S. Pat. No. 5,405,531 to Hitzman et al. discloses that in aqueous systems containing denitrifying bacteria and sulfate-reducing bacterial (SRB), the amount of hydrogen sulfide present can be reduced and the formation of hydrogen sulfide can be prevented by introducing nitrite and nitrate and/or molybdate to the aqueous system. The denitrifying organisms compete with the sulfate-reducing bacteria for the available carbon nutrients, thus preventing the SRB from producing hydrogen sulfide already present in the system. Also taught is that the molybdate and nitrite ions inhibit or kill the sulfate-reducing bacteria. This technology regarding the prevention of hydrogen sulfide production has been referred to as "Biocompetitive Exclusion" (Hitzman, D. O. and Dennis, D. M., "New Technology for Prevention of Sour Oil and Gas", SPE Paper 37908, Paper presented at the SPE/EPA Exploration and Production Environmental conference, Dallas Tex., Mar. 3—5, 1997). The indigenous anaerobic microbial consortium, which includes heterotrophic denitrifiers and anaerobic Thiobacillus species, which includes heterotrophic denitrifiers and anaerobic Thiobacillus species, will rapidly respond to the introduction of alternate electron acceptors such as nitrate, which are more active than sulfate. Their prolific growth results in faster and complete utilization of the volatile fatty acids, thereby denying this carbon source to the sulfate-reducing bacteria. Thus, selective addition of water-soluble inorganic nutrient formulations that include nitrate and nitrite can prevent the deleterious activity of the sulfate-reducing bacteria.

Reinsel, et al. (Reinsel, M. A., Sears, J. T., Stewart, P. S. and McInerney, M. J, "Control of microbial souring by nitrate, nitrite or gluteraldehyde injection in a sandstone column, "*Journal of Industrial Microbiology*, 17, p. 128, 1996) determined that sulfide production could be inhibited from two different oilfield produced water consortia containing active sulfate-reducing and denitrifying (nitrate-reducing) bacteria in crushed Berea sandstone columns with the addition of nitrate. They attributed this result to the inhibition of sulfate reduction due to presence of nitrite, an intermediate of nitrate reduction, which is a known microbial inhibitory agent. They also determined that the direct addition of very low levels of nitrite inhibit $H_2S$ production successfully.

While all of the foregoing methods for inhibiting the formation of $H_2S$ and for removing $H_2S$ are effective to some extent, none is wholly satisfactory because the efficiency of each is low and the relative cost of utilizing them is quite high. For that reason, applicants have sought an efficient and more cost-effective method for keeping the $H_2S$ level of wastewater streams down to a safe level by a method which involves both keeping the production of $H_2S$ production low and removing whatever low amount of $H_2S$ is produced.

SUMMARY OF THE INVENTION

Therefore, in its primary aspect, the invention is directed to a synergistic method for reducing the amount of hydrogen sulfide contained in municipal, oilfield, and other industrial water streams containing both sulfate-reducing bacteria and $H_2S$-metabolizing bacteria comprising adding to the water stream metal nitrate and/or metal nitrite, to provide a source of nitrogen for the $H_2S$-metabolizing bacteria, and finely divided particles of polycyclic quinone to inhibit the production of $H_2S$ by the sulfate-reducing bacteria.

The function of the polycyclic quinone is to inhibit the ability of the sulfate-reducing bacteria to reduce sulfate to hydrogen sulfide by blocking the production of adenosine triphosphate by the sulfate-reducing bacteria, thereby removing the bacteria's ability to respire via sulfate reduction. Without sulfate reduction, the bacteria do not produce hydrogen sulfide.

The function of the nitrate and/or nitrite is to stimulate the rapid growth of the heterotrophic denitrifiers and anaerobic Thiobacillus species populating the waters, thereby allowing these bacteria to outcompete sulfate-reducing bacteria for available nutrients, thus reducing the ability of the sulfate-reducing bacteria to grow and be active. An intermediate product of nitrate reduction is nitrite, which itself is a known inhibitor of microbes. In addition, heterotrophic denitrifiers and Thiobacillus species are capable of oxidizing sulfide back to sulfate, thereby reducing the amount of $H_2S$ already present in the waters and any new $H_2S$ generated by sulfate-reducing bacteria untreated with the polycyclic quinone.

In particular, the invention is directed to a method for a method for reducing the level of hydrogen sulfide ($H_2S$) in water of pH 4–10, having dispersed therein indigenous amounts of sulfate-reducing bacteria and $H_2S$-metabolizing bacteria, comprising adding to the $H_2S$-containing water:

(1) finely divided particles of polycyclic quinone selected from anthraquinone, anthrahydroquinone and mixtures thereof, the average size of the particles being no greater than 10 micrometers, which particles are applied as an aqueous dispersion of (a) water-insoluble non-ionic particles suspended in an aqueous medium, or (b) an alkaline solution of an ionic salt of the polycyclic quinone having a pH at least 2 pH units higher than the alkaline ionic salt solution, which salt is thereby converted to the corresponding water-insoluble, non-ionic polycyclic quinone particles upon exposure to the lower pH of the $H_2S$-containing water, and (2) an aqueous solution of metallic nitrogen oxide selected from the group consisting of metal nitrate, nitrite and mixtures thereof, the weight ratio of polycyclic quinone to metallic nitrogen oxide being (3–30)× $10^{-3}$, and the amount of the polycyclic quinone and nitrogen oxide added to the $H_2S$-containing water being sufficient to increase its oxidation-reduction potential (ORP) to a preselected higher level.

DEFINITIONS

As used herein, with respect to the accessibility of sulfate-reducing bacteria and hydrogen sulfide-metabolizing bacteria to the flowing water stream or water within a tank or vessel, the term "containing" includes both bacteria in the bulk water as well as bacteria within any biofilm formed on the inner surface of the conduit, tank or vessel within which the water is flowing or stationary.

Within the context of the invention, "wastewater" is defined as those waters from municipal, oilfield and industrial operations containing sulfate-reducing bacteria and denitrifying (nitrate-reducing) bacteria and which are susceptible to generation of biogenic $H_2S$ due to the growth and activity of the sulfate-reducing bacteria. They include water streams resulting from municipal use, petroleum and natural gas production operations, seawater used in oilfield waterflood operations, effluent waters from chemical and biochemical processing and paper and pulp operations, and water used in industrial heat transfer operations.

The following abbreviations used herein are defined as follows:

| ADWF | average dry weather flow |
|------|--------------------------|
| AQ   | anthraquinone            |
| G/D  | gallons per day          |
| Lbs/D | pounds per day          |
| MG/D | million gallons per day  |
| mg/L | milligrams per liter     |
| ppm  | parts per million by weight; and |
| PCQ  | polycyclic quinone.      |

DETAILED DESCRIPTION OF THE INVENTION

A. In General

It is recognized, in a very general sense, that each of the added reactants to water systems treated in accordance with the invention perform a function for which they are previously known. However, applicants have discovered that when these reactants are used together, whether simultaneously or sequentially, they function in a highly synergistic manner. That is, both the degree of bacterial inhibition by the polycyclic quinones and the extent of $H_2S$ consumption resulting from nitrate addition are improved far beyond that level which can be obtained by either technique by itself.

Furthermore, an important advantage of the method of the invention is that no separation step is required in handling the treated water. Both the inhibition of $H_2S$ formation and the metabolism of the $H_2S$ are accomplished without the necessity of separating either the reactants or the by-products of the reaction products from the treated water system.

B. Polycyclic Quinones

Unlike biocides, which are aimed at killing sulfate-reducing bacteria, the polycyclic quinones used in this invention only inhibit their activity. Studies have shown that the polycyclic quinones block the production of adenosine triphosphate by the bacteria, thereby removing the bacteria's ability to respire via sulfate reduction. Without sulfate reduction, $H_2S$ cannot be produced by the bacteria. Nevertheless, the polycyclic quinones have no adverse affect on the $H_2S$-metabolizing bacteria.

1. Composition: A substantial number of polycyclic quinones can be used in the invention. As used herein, the term "polycyclic quinone" refers to tricyclic condensed ring quinones and hydroquinones, as well as water-soluble precursors thereof. On the whole, the non-ionic polycyclic quinones and polycyclic hydroquinones (herein referred to collectively as PCQs) have very low solubility in water at ambient temperatures. For use in the invention, it is preferred that such PCQs have a water solubility no higher than about 1,000 ppm by weight. Thus, suitable PCQs for use in the method of the invention are those water-insoluble, nonionic polycyclic quinones selected from anthraquinones and anthrahydroquinones and mixtures thereof, which have up to four substituent groups selected from methyl, methoxyl, hydroxyl, carboxyl and amino groups.

However, as noted above, certain precursors of such PCQs can also be used in the invention, either combined with the relatively insoluble PCQs or by themselves. Such precursors are anionic salts of PCQs, which salts are water-soluble under alkaline anaerobic conditions. However, these materials are not stable and are easily converted to the insoluble quinone form by exposure to lower alkalinity or non-alkaline aqueous solutions or to a source of oxygen. Thus, in the use of these materials in water systems containing sulfate-reducing bacteria and nitrate-metabolizing bacteria, the PCQs will ordinarily be exposed to low pH conditions that readily convert the unstable alkaline salts to the more stable non-ionic quinone form.

Among the many water-insoluble PCQs which can be used in the invention are anthraquinone, phenanthrene-quinone and the alkyl, alkoxy and amino derivatives of such quinones, anthraquinone-1,2-naphthacridone, 1,2-benzanthraquinone, 2,7-dimethylanthraquinone, 2-methylanthraquinone, 3-methylanthraquinone, 2-aminoanthraquinone and 1-methoxyanthraquinone. Of the foregoing cyclic ketones, anthraquinone and methylanthraquinone are preferred because they appear to be more effective. Naturally occurring anthraquinones can be used as well as synthetic anthraquinones.

Other PCQs which can be used include insoluble anthraquinone compounds, such as 1,8-dihydroxy-anthraquinone, 1-amino-anthraquinone, 1-chloro-anthraquinone, 2-chloro-anthraquinone, 2-chloro-3-carboxyl-anthraquinone, 1-hydroxyanthraquinone and unsubstituted anthraquinone. Various ionic derivatives of these materials can be prepared by catalytic reduction in aqueous alkali.

In addition, a wide variety of anthrahydroquinone compounds can be used in the method of the invention. As used herein, the term "anthrahydroquinone compound" refers to compounds comprising the basic tricyclic structure such as 9,10-dihydroanthrahydroquinone, 1,4-dihydroanthrahydroquinone, and 1,4,4$a$,9$a$-tetrahydroanthrahydroquinone. Anthrahydroquinone itself is 9,10-dihydroxyanthracene.

More particularly, both water-insoluble and water-soluble forms can be used. The non-ionic compounds are largely insoluble in aqueous systems, while ionic derivatives, such as di-alkali metal salts, are largely soluble in water. The water soluble forms are stable only in high pH anaerobic fluids. Low pH fluids (pH less than about 9–10) will result in the formation of the insoluble molecular anthrahydroquinone. Anthrahydroquinone treatments are, therefore, usually implemented with the soluble ionic form in a caustic solution. Sodium hydroxide solutions are preferred over the hydroxides of other alkali metals for economic reasons.

2. Configuration: Because many of the sulfate-reducing bacteria contained in wastewater systems are found in biofilms formed on the periphery of the wastewater vessels and conduits, it is necessary that the polycyclic quinones be able to penetrate into the biofilms at low dosages without undergoing reaction.

The extraordinary effectiveness of various forms of anthraquinone lies in their non-reactivity. These products are transported into the biofilm, diffuse through the biofilm voids, and then diffuse or are randomly transported by Brownian motion into the bacterial microcolonies without reduction in concentration as a consequence of a reaction with biofilm constituents. These anthraquinone materials are unaffected by other bacteria or the exopolysaccharide matrix present in the biofilm.

Even though solid particles of polycyclic quinone (PCQ) are required to inhibit the sulfate-reducing bacteria activity, the PCQ can be introduced into the microbial environment in several physical forms. The PCQ can be introduced as a dispersion of these solid particles while an ionic (alkali metal salt) form of the PCQ will allow it to be solubilized in an anaerobic caustic solution with pH greater than 12 and preferably greater than 13. The salt stays soluble if the pH of the solution remains above about 12, with precipitation of solid PCQ taking place as the pH is reduced below this value. In the soluble form or with a slight amount of precipitated PCQ (typically in colloidal form), anthraquinone is in molecular form or extremely small (submicron-sized) particles. The PCQ molecules or colloidal particles will then be able to move freely in the biofilm, contacting sulfate-reducing bacteria cells easily. Contact of PCQ with the sulfate-reducing bacteria and partitioning of the PCQ into the cell membrane blocks the organism's adinosine triphosphate production. In addition, decreases in pH in the biofilm (due to acid production from other bacteria in the biofilm or due to a sweeping of lower pH fluid through the pipe) will precipitate more small PCQ particles from the solution within the biofilm. This will expose the sulfate-reducing bacteria within the biofilm to additional PCQ particles, furthering the efficacy of the anthraquinone treatment. When the PCQ added to the wastewater is in the form of a suspension of finely divided particles, it is preferred that their largest dimension be no greater than 50 micrometers, and preferably no greater than 5–10 micrometers so that they can more easily pass through biofilm.

Notwithstanding the fact that the active species seems to be the insoluble form of anthraquinone, it is nevertheless preferred to use the ionic (water-soluble) anthraquinone form because it diffuses into the biofilm and thus contacts the sulfate-reducing bacteria more readily. The activity of the ionic form of the anthraquinone seems to be derived from its conversion from the ionic form to the non-ionic form, by which it is precipitated as very fine particles which attach to the sulfate-reducing bacteria.

Whether the soluble or insoluble anthraquinone is used, it has been observed that the functional attachment of the anthraquinone particles to the bacteria is limited in time by metabolism of the particles by the sulfate-reducing bacteria. Thus, application of the treating medium must be repeated periodically in order to maintain inhibition effectiveness.

C. Methods of Operation

The customary method for carrying out nitrate and/or nitrite addition in waste water systems is continuous addition to a flowing waste water stream. Usually this is done with aqueous solutions of the metal nitrate and/or nitrite. Because of their ease in handling, nominal 50% wt. aqueous solutions of the calcium salt are frequently used for this purpose. On the other hand, the addition of PCQ or precursors thereof in accordance with the invention can be carried out in a variety of ways. For example, nitrate/nitrite addition can be stopped, and the PCQ then added to the water stream periodically as a slug dose over a short duration in an amount sufficient to be effective for an extended time, after which nitrate/nitrite addition is resumed as soon as PCQ addition is completed. A further method is to add the PCQ continuously to the water either by admixing it with the nitrate/nitrite solution or by adding the PCQ directly to the water stream simultaneously with the nitrate/nitrite. For ease in metering, the metal nitrate/nitrite is usually added in aqueous solution. The PCQ is added as an aqueous suspension of finely divided PCQ particles. When PCQ precursors are used, they are added in the form of an aqueous solution of alkali metal salts in a caustic solution.

Even though intermittent addition of the polycyclic quinone to the nitrate/nitrite-containing water is quite satisfactory, it has been found that continuous addition is more efficient with respect to sulfide removal. Therefore, continuous addition of the polycyclic quinone is preferred.

Because most of the sulfate-reducing bacteria are found in the biofilms on the inner surface of pipelines through which the waters are flowing, the amount of PCQs required in the absence of nitrate and/or nitrite treatments to reduce the amount of $H_2S$ produced in those biofilms is, for a specific application, approximately proportional to the area of the inside surfaces of the pipelines. Each type of application requires different amounts of polycyclic quinones due to the differing conditions of the biofilm. We have found that municipal wastewater pipelines (i.e., sewer conduits) usually require more PCQ per unit surface area than oilfield seawater pipelines because the sewers are usually more heavily fouled with biomass. Consequently, while it has been found that the level of PCQ or precursor addition per batch treatment should be 0.1–0.5 lbs. per treatment for each 1,000 sq. ft. of seawater pipeline, while as much as 1–5 lbs. For each 1,000 sq. ft. of sewer conduit inner surface is required. Optimum usage of PCQ addition is obtained at 0.2–0.3 lbs. per treatment for each 1,000 sq. ft. of seawater pipeline (sewer conduit) surface area. Suitable treatment frequency for PCQs is a function of the biofilm condition, the condition of the environment (e.g., temperature), and the microbial nutrient content in the flowing water. We have found that monthly treatments are sufficient for some applications while daily treatments are required for more difficult applications. During each batch treatment, a predetermined amount of PCQ, based on the total surface area to be treated, is injected into the water system over a period of several minutes to several hours at a concentration in the water between about 1 and 2000 mg/L. (The product of PCQ concentration, water flow rate and treatment time is equal to the total amount of PCQ added.)

The use of nitrate and/or nitrite treatments alone to control $H_2S$ in water systems is based on the total amount of $H_2S$ produced in an untreated system. Although the dosage rate for a municipal wastewater system might be as low as 30–50 gallons of 50% wt. calcium nitrate solution per million gallons of wastewater, many difficult-to-treat systems require several hundred gallons of nitrate solution per million gallons of water.

Due to the synergistic result when both PCQs and nitrate and/or nitrite solutions are used to treat a water system, lower amounts of each compound may be used. It has been found that the volume of nitrate and/or nitrite solution that may be used is reduced by 20–60% when PCQ co-treatments are applied at 10–20% the rate required in the absence of nitrate and/or nitrite treatments.

EXAMPLES

Example 1

A series of tests was carried out in an urban wastewater system among three vacuum collection systems (Stations A, B and C) connected by 6 inch diameter pipe. The distance between Stations A and B was 5,218 feet and the distance between Stations B and C was 2,453 feet. Normal wastewater flow between Stations A and B is 138–180 thousand gallons per day and normal flow between Stations B and C is 367–430 thousand gallons per day.

This segment of the wastewater system is normally treated with 80 gallons per day of nitrate to remove hydrogen sulfide, by which the level $H_2S$ is reduced to 1 mg/L.

For purposes of this test, the above-described parts of the wastewater system were operated for seven days without the addition of either nitrate or anthraquinone (AQ). At the end of the seven days, the ORP of the system was −153 and $H_2S$ level of 5.6 ppm.

Upon completion of the above-described seven-day test, in which no action was made to remove $H_2S$, an aqueous dispersion containing 50% wt. anthraquinone was added to the system periodically at the rate of 6.5 gallons per day for a period of six days. At the end of the six day period, the ORP of the system was −151 and the $H_2S$ level was reduced to 4.0 ppm.

Following the above six day test using only anthraquinone for treatment, the addition of anthraquinone was stopped and continuous nitrate addition to the system was resumed at a level only ten percent of the previous rate of addition. That is, only 8 gallons of nitrate solution was added daily instead of the previous level of 80 gallons daily. Interestingly, During the 11 days following resumption of nitrate addition during which anthraquinone addition was discontinued altogether, the ORP of the wastewater dropped to zero and the $H_2S$ level in the system dropped to 0.8 ppm.

Addition of AQ is now made once per month and $H_2S$ is still at the 0.8–1.0 ppm level, which is considered acceptable. The cost savings to the municipality more than paid for the use of AQ. A continued use of only 8 gallons of nitrate per day indicates continued synergy between the reactants.

Example 2

A test was conducted in a lift station of a community wastewater system discharging about 75,000 gallons/day (284,000 L/day) of waste water into an eight inch force main discharging 2,550 feet downstream into a gravity collection line. Without the addition of materials to control the hydrogen sulfide level, the level of hydrogen sulfide in the waste water stream was 30 mg/L. By addition of 18 gallons/day (68 L/day) of sodium nitrate solution alone, the hydrogen sulfide in the discharge was maintained at 0.95 mg/L. While continuing the addition of nitrate solution, the flowing stream was dosed with forty pounds of alkaline (pH 11) anthraquinone over the course of a few minutes and the addition of sodium nitrate was reduced to 5.5 gallons/day (21 L/day). At the end of two weeks, the sulfide level was only 0.82 mg/L. Two weeks after the initial addition of PCQ, forty pounds of nitrate solution were again added to the flowing stream and the daily addition of nitrate was continued. The hydrogen sulfide level from the gravity collection line during the subsequent two week period remained at about the same level. These data show clearly the synergistic action of periodic PCQ addition in combination with continuous nitrate addition.

Example 3

A one million gallon/day effluent water stream from a bioprocessing plant contains a microbial consortium including sulfate-reducing and denitrifying bacteria, organic nutrients and metabolic products, and sulfate ions. This stream is extremely susceptible to the generation of biogenic hydrogen sulfide due to the favorable environment for the growth of the sulfate-reducing bacteria. The stream leaving the plant already contains 5 mg/L sulfide and, if left untreated, the sulfide level increases to 20 mg/L at the end of the 18-inch diameter, 5 mile long pipe transporting the effluent to the water treatment plant. This sulfide level was extremely high and caused odor complaints at the outflow and concerns about the toxic effects of hydrogen sulfide. A standard treatment for this effluent stream is to inject 150 gallons per day continuously of a 45 weight percent calcium nitrate solution. This treatment causes an increase in denitrifying bacteria activity, which results in the metabolic oxidation of sulfide. The outflow water is maintained at an elevated sulfide level of 7 mg/L with this continuous 24 hour/day treatment. A second standard treatment is to inject 60 gallons of a 10 weight percent disodium anthrahydroquinone solution once per week as a slug over a 60 minute duration. This treatment results in the deposition of colloidal-sized anthrahydroquinone particles in the biofilm on the pipe wall and the subsequent inhibition of sulfate reduction and sulfide generation by the sulfate-reducing bacteria. The outflow water contains 5 mg/L of sulfide shortly after the anthrahydroquinone treatment is begun and slowly increases to 7 mg/L prior to the next weekly treatment. The preferred treatment of this effluent water as per the invention is to inject a 30 gallon slug of anthrahydroquinone disodium salt solution over a period of a 30 minute duration once per week while continuously injecting 50 gallons/day of calcium nitrate solution. This combined treatment causes a synergistic result whereby the biogenic sulfide generation is reduced significantly and sulfide present in the water is consumed. The outflow water sulfide content is maintained at 2 mg/L shortly after the resumption of the nitrate treatment following the anthrahydroquinone treatment and slowly increases to 5 mg/L by the end of the one-week cycle. This preferred treatment is not only cost effective, compared to either of the two individual treatments, but also is technically favorable since the sulfide content of the outflow water is reduced over that of the influent.

Example 4

A series of experiments was conducted in the laboratory to observe the synergy obtained with the combined use of calcium nitrate and anthraquinone to inhibit hydrogen sulfide generation in samples of pulp mill effluent (PME) water which contained an active population of sulfate-reducing and denitrifying bacteria.

Pulp mill effluent (PME) water samples were obtained from a pulp mill in East Texas. These samples were stored at about 5 C. to control bacteria growth. Experiments were performed by almost filling 12 mL glass culture tubes with PME and then treating the PME with calcium nitrate solution, aqueous anthraquinone dispersion, or combinations of the two. Untreated controls were also run. The culture tubes were capped tightly and the contents were incubated at 50 C. while being continuously agitated. Preliminary studies indicated that incubating the untreated PME at 50 C. would produce significant $H_2S$ generation in about three days. Enough culture tubes were used so that the contents of multiple tubes could be analyzed daily for total sulfide and then discarded.

Table 1 summarizes the results from several sets of tests using 50% wt. calcium nitrate solutions and/or 50% wt. aqueous anthraquinone dispersions to treat the PME. Each data point represents the average % inhibition of sulfide production obtained from analyses of multiple tubes. The % inhibition is related to the amount of sulfide produced from untreated controls during that same set of tests. These results show that neither 25 ppm of the calcium nitrate solution nor 2 ppm of the anthraquinone dispersion were sufficient by themselves to inhibit sulfide generation significantly for 5 days or longer. However, tests with a combined treatment of 25 ppm of the calcium nitrate solution plus 2 ppm of the anthraquinone dispersion significantly inhibited sulfide production for 6 days. These test results clearly show that there is a synergy obtained with the combined use of calcium nitrate and anthraquinone when treating pulp mill effluents for the control of $H_2S$ production.

TABLE 1

RESULTS FROM LABORATORY STUDY SHOWING SYNERGY OF CALCIUM NITRATE AND ANTHRAQUINONE TREATMENTS TO INHIBIT $H_2S$ PRODUCTION IN PULP MILL EFFLUENT WATERS.

| Calcium Nitrate Solution, mg/L | AQ Dispersion, mg/L | % Inhibition of Sulfide Production vs. Days Following Test Start | | | | | |
|---|---|---|---|---|---|---|---|
| | | 3 | 4 | 5 | 6 | 7 | 8 |
| 25 | 0 | 22.2 | 11.1 | 28.0 | 0.0 | 9.1 | 22.2 |
| 50 | 0 | 33.3 | 20.0 | 26.0 | 0.0 | 27.3 | 22.2 |
| 50 | 0 | 63.0 | 84.0 | 0.0 | 25.4 | | |
| 50 | 0 | | 22.2 | 35.2 | 85.5 | 52.9 | |
| 200 | 0 | | 97.8 | 66.7 | 98.2 | 98.8 | |
| 200 | 0 | 96.9 | 95.1 | 48.2 | 88.8 | | |
| 1000 | 0 | | 100.0 | 100.0 | 100.0 | 100.0 | |
| 0 | 2 | 68.9 | 81.1 | 30.0 | 37.5 | 9.1 | 11.1 |
| 0 | 5 | 93.3 | 91.1 | 64.0 | | 92.7 | 93.3 |
| 0 | 10 | 67.8 | 95.6 | 82.7 | 90.0 | 94.5 | 97.8 |
| 0 | 10 | 93.8 | 91.4 | 39.3 | 3.0 | | |
| 0 | 20 | 89.7 | 85.2 | 85.7 | 98.5 | 83.9 | |
| 0 | 50 | | 92.2 | 93.8 | 96.4 | 96.5 | |
| 0 | 50 | 89.7 | 88.9 | 67.9 | 94.0 | 93.5 | |
| 0 | 200 | | 90.0 | 93.8 | 93.6 | 92.9 | |
| 0 | 1000 | 92.2 | 99.5 | 95.9 | 96.5 | | |
| 25 | 2 | 93.9 | 88.3 | 83.8 | 84.5 | 36.2 | |

Example 5

A test was carried out in an urban wastewater system among three vacuum collection systems (Stations A, B and C) connected by 6 inch diameter pipe. The distance between Stations A and B was 5,218 feet and the distance between Stations B and C was 2,453 feet. Normal wastewater flow between Stations A and B is 138–430 thousand gallons per day. This wastewater system is normally treated with 80 gallons per day of a 50% wt. aqueous calcium nitrate solution to reduce the hydrogen sulfide level to about 1 mg/L.

To initiate the test, the wastewater system was operated for seven days without the addition of calcium nitrate. At the end of the seven days, the ORP of the system was −153 mv and the $H_2S$ level was 5.6 mg/L. At this time an aqueous dispersion containing 50% wt. anthraquinone particles was added to the system periodically at the rate of 65 pounds per day for a period of six days. At the end of the six-day period, the oxidation-reduction potential (ORP) of the system was −151 mv and the $H_2S$ level was reduced to 4.0 mg/L.

Following the six-day period using only anthraquinone for treatment, the addition of anthraquinone was stopped and continuous calcium nitrate addition to the system was resumed at a level of only 8 GPD instead of the previous level of 80 GPD. Interestingly, during the 11 days following resumption of calcium nitrate addition, during which anthraquinone addition was discontinued altogether, the ORP of the wastewater increased to about zero and the $H_2S$ level in the system dropped to 0.8 mg/L.

Addition of AQ is now made only once per month and the $H_2S$ is still at the 0.8–1.0 mg/L level, which is considered acceptable. The cost savings to the municipality more than paid for the use of AQ. The use of only 8 gallons of calcium nitrate solutions per day with monthly AQ additions indicates continued synergy between the reactants.

Example 6

A test was conducted in a lift station of a community wastewater system discharging about 75,000 gallons/day of wastewater into an eight inch force main discharging 2,550 feet downstream into a gravity collection line. Without the addition of materials to control the $H_2S$ level, the level of $H_2S$ in the wastewater stream was 30 mg/L. With the addition of 18 gallons/day of 50% wt. calcium nitrate solution alone, the hydrogen sulfide in the discharge was maintained at 0.95 mg/L. While continuing the addition of calcium nitrate solution, the wastewater was slug-dosed over several minutes with anthraquinone by adding forty pounds of an aqueous dispersion containing 50% wt. anthraquinone particles into a wet well which also was dosed with enough sodium hydroxide solution to increase the water pH to 11. The calcium nitrate injection rate was also reduced to 5.5 gallons/day. At the end of two weeks, the $H_2S$ level at the discharge was only 0.82 mg/L. At this time another forty pound slug—dose of the anthraquinone dispersion was added to the flowing stream while continuing the daily addition of calcium nitrate. The $H_2S$ level from the gravity collection line during the subsequent two-week period remained at about the same level. These data show clearly the synergistic action of periodic AQ addition in combination with continuous nitrate addition.

Example 7

A 24-inch diameter force main located in a Southern California city, having an AWDF of 3.2 MG/D, was treated continuously with 194 G/D of a 50% wt. aqueous solution of calcium nitrate. After several days of such treatment, the $H_2S$ level in the liquid at the outfall of the main was measured at 1.36 mg/L. At that time, the rate of calcium nitrate addition was reduced to 140 G/D and continuous addition of an aqueous suspension of finely divided particles of anthraquinone was made to the following wastewater at an average daily rate of 3 pounds per day.

As shown by the data in Table 2 below, this quite small addition of AQ to the liquid flow resulted in a 64% reduction of $H_2S$ from the system, as compared with treatment by nitrate alone, even though the rate of nitrate addition had itself been reduced by 28%. Based on prior experience in similar systems, it would require an anthraquinone addition rate of about 26 pounds per day to reduce the sulfide to such a low level in the absence of nitrate addition. Therefore, it is clear that the nitrate and AQ are interacting with a substantial degree of synergy.

Example 8

A 36-inch force main located in Fulton County, Georgia, having an ADWF of 4.5 million MG/D, was treated continuously with 440 G/D of a 50% wt. aqueous solution of calcium nitrate. After several days of such treatment, the $H_2S$ in the water at the outfall of the main was measured at 1.2 mg/L. At this time, the rate of calcium nitrate addition was reduced to 280 G/D and addition of an aqueous suspension of finely divided particles of AQ was made continuously to the flowing wastewater at a daily average rate of 5.6 pounds per day.

As shown by the data in Table 2, this quite small addition of anthraquinone to the liquid flow resulted in substantially complete removal of hydrogen sulfide from the liquid in the system even though the rate of nitrate addition had been reduced by 36%. Based on prior experience in similar wastewater systems, it would require an anthraquinone addition rate of about 37 pounder per day to reduce the $H_2S$ to such a low level in the absence of nitrate. It is therefore again clear that the nitrate and AQ are producing a highly synergistic change in the composition of the wastewater bio-system.

Example 9

A further test of the invention was carried out in an integrated collection system located in a metropolitan area of Minnesota, comprising four sequenctial force mains of different lengths having diameters of 12 inches, 16 inches, 18 inches and 24 inches. The total ADWF of the system was 1.65 MG/D. This system was treated continuously with 260 GPD of a 50% wt. calcium nitrate solution, and, after several days, the $H_2S$ level at the outfall of the last force main was measured at 2.6 mg/L. The level of calcium nitrate addition was then reduced to 130 GPD and an addition of a 50% wt. aqueous suspension of finely divided particles of anthraquinone was made continuously to the flowing wastewater at a rate of 2.6 pounds per day.

Example 10

A series of experiments was conducted in the laboratory to observe the synergy obtained with the combined use of calcium nitrate and anthraquinone to inhibit hydrogen sulfide generation from samples of pulp mill effluent (PME) water which contained an active population of sulfate-reducing and denitrifying bacteria.

Pulp mill effluent water samples were obtained from a pulp mill in East Texas. These samples were stored at about 5 C. to control bacteria growth. Experiments were performed by almost filling 12 mL glass culture tubes with PME and then treating the PME with calcium nitrate solution, aqueous anthraquinone dispersion, or combinations of the two. Untreated controls were also run. The culture tubes were capped tightly and the contents were incubated at 50° C. while being continuously agitated. Preliminary studies indicated that incubating the untreated PME at 50 C. would result in significant $H_2S$ generation in about three days. Enough tubes were used so that the contents of multiple tubes could be analyzed daily for total sulfide and then discarded.

Table 3 summarizes the results from several sets of tests using 50% wt. calcium nitrate solutions and/or 50% wt. aqueous anthraquinone dispersions to treat the PME. Each datum point represents the average % inhibition of sulfide production obtained from analyses of multiple tubes, where the % inhibition is related to the amount of sulfide produced from untreated controls during that same set of tests. These results show that neither 25 ppm of the calcium nitrate solution nor 2 ppm of the anthraquinone dispersion was sufficient by themselves to inhibit significant sulfide generation for 5 days or longer. However, tests with a combined treatment of 25 ppm of the calcium nitrate solution plus 2 ppm of the anthraquinone dispersion significantly inhibited sulfide production for 6 days. These test results clearly show that there is a synergy obtained with the combined use of calcium nitrate and anthraquinone when treating pulp mill effluents for the control of $H_2S$ production.

TABLE 2

USE OF POLYCYCLIC QUINONE TO AUGMENT EFFICIENCY OF NITRATE TREATMENT OF WASTEWATER

| Example No. | ADWF (MG/D) | Ca(NO$_3$)$_2$ Solution[1] (G/D) | AQ (lbs/D) | Ca(NO$_3$)$_2$ Reduction (%) | Aqueous $H_2S$ (mg/L) | $H_2S$ Reduction (%) |
|---|---|---|---|---|---|---|
| 3 | 3.2 | 194 | none | — | 1.36 | — |
|   | 3.2 | 140 | 3 | 28 | 0.49 | 64 |
|   | 3.2 | none | 26[2] | 100 | 0.49 | 64 |
| 4 | 4.5 | 440 | none | — | 1.2 | — |
|   | 4.5 | 280 | 5.6 | 36 | bdl[3] | >99 |
|   | 4.5 | none | 37[2] | 100 | bdl[3] | >99 |
| 5 | 1.65 | 260 | none | — | 2.6 | — |
|   | 1.65 | 130 | 2.6 | 50 | bdl[3] | >99 |
|   | 1.65 | none | 14[2] | 100 | bdl[3] | >99 |

[1]50% wt. aqueous solution;
[2]Estimate, based on previous experience, to attain stated $H_2S$ reduction;
[3]Below detectable limit.

TABLE 3

RESULTS FROM LABORATORY STUDY SHOWING SYNERGY OF CALCIUM NITRATE AND ANTHRAQUINONE TREATMENTS TO INHIBIT $H_2S$ PRODUCTION IN PULP MILL EFFLUENT WATERS.

| Calcium Nitrate Solution, mg/L | AQ Dispersion, mg/L | % Inhibition of Sulfide Production vs. Days Following Test Start | | | | | |
|---|---|---|---|---|---|---|---|
| | | 3 | 4 | 5 | 6 | 7 | 8 |
| 25 | 0 | 22.2 | 11.1 | 28.0 | 0.0 | 9.1 | 22.2 |
| 50 | 0 | 33.3 | 20.0 | 26.0 | 0.0 | 27.3 | 22.2 |
| 50 | 0 | 63.0 | 84.0 | 0.0 | 25.4 | | |
| 50 | 0 | | 22.2 | 35.2 | 85.5 | 52.9 | |
| 200 | 0 | | 97.8 | 66.7 | 98.2 | 98.8 | |
| 200 | 0 | 96.9 | 95.1 | 48.2 | 88.8 | | |
| 1000 | 0 | | 100.0 | 100.0 | 100.0 | 100.0 | |
| 0 | 2 | 68.9 | 81.1 | 30.0 | 37.5 | 9.1 | 11.1 |
| 0 | 5 | 93.3 | 91.1 | 64.0 | | 92.7 | 93.3 |
| 0 | 10 | 67.8 | 95.6 | 82.7 | 90.0 | 94.5 | 97.8 |
| 0 | 10 | 93.8 | 91.4 | 39.3 | 3.0 | | |
| 0 | 20 | 89.7 | 85.2 | 85.7 | 98.5 | 83.9 | |
| 0 | 50 | | 92.2 | 93.8 | 96.4 | 96.5 | |
| 0 | 50 | 89.7 | 88.9 | 67.9 | 94.0 | 93.5 | |
| 0 | 200 | | 90.0 | 93.8 | 93.5 | 92.9 | |
| 0 | 1000 | 92.2 | 99.5 | 95.9 | 96.5 | | |
| 25 | 2 | 93.9 | 88.3 | 83.8 | 84.5 | 36.2 | |

What is claimed is:

1. A method for reducing the level of hydrogen sulfide ($H_2S$) in water of pH 4–10, having dispersed therein indigenous amounts of sulfate-reducing bacteria and $H_2S$-metabolizing bacteria, comprising adding to the $H_2S$-containing water:
   (a) finely divided particles of polycyclic quinone selected from anthraquinone, anthrahydroquinone and mixtures thereof, the average size of the particles being no greater than 10 micrometers, which particles are applied as an aqueous dispersion of (a) water-insoluble non-ionic particles suspended in an aqueous medium or (b) an alkaline solution of an ionic salt of the polycyclic quinone having a pH at least 2 pH units higher than the $H_2S$-containing water, which salt is thereby converted to the corresponding water-insoluble, non-ionic polycylic quinone particles upon exposure to the lower pH of the $H_2S$-containing water and
   (b) an aqueous solution of metallic nitrogen oxide selected from the group consisting of metal nitrate, nitrite and mixtures thereof, the weight ratio of polycyclic quinone to metallic nitrogen oxide being (3–30)×

$10^{-3}$, and the amount of the polycyclic quinone and nitrogen oxide added to the $H_2S$-containing water being sufficient to increase its oxidation-reduction potential (ORP) to a preselected higher level.

2. The method of claim 1 in which the polycyclic quinone is dispersed in the aqueous solution of metallic nitrogen oxide.

3. The method of claim 2 in which the polycyclic quinone is added to the $H_2S$-containing water in the form of non-ionic particles dispersed in the aqueous solution of metallic nitrogen oxide.

4. The method of claim 2 in which the polycyclic quinone is added to the $H_2S$-containing water in the form of ionic compounds dissolved in the aqueous alkaline solution of the metallic nitrogen oxide.

5. The method of claim 2 or in which the water is contained in a vessel or conduit, the inner walls of which bear a layer of biofilm in contact with the contained water.

6. The method of claim 1 in which the treated water is quiescent.

7. The method of claim 1 in which the treated water is flowing.

8. The method of claim 1 in which the size of the water-insoluble particles in step (b) is no greater than 2 micrometers.

9. The method of claim 1 in which the preselected ORP level is at least about −50 mv.

* * * * *